United States Patent
Flodin et al.

(10) Patent No.: US 6,627,258 B1
(45) Date of Patent: Sep. 30, 2003

(54) FILM FOR MEDICAL USE, CONSISTING OF LINEAR BLOCK POLYMERS OF POLYURETHANE AND A METHOD FOR THE PRODUCTION OF SUCH A FILM

(75) Inventors: Per Flodin, Hovås (SE); Katrin Gisselfält, Göteborg (SE)

(73) Assignee: Artimplant AB (SE)

( * ) Notice: Subject to any disclaimer, the term of this patent is extended or adjusted under 35 U.S.C. 154(b) by 0 days.

(21) Appl. No.: 09/890,291

(22) PCT Filed: Jan. 18, 2000

(86) PCT No.: PCT/SE00/00084

§ 371 (c)(1),
(2), (4) Date: Jul. 27, 2000

(87) PCT Pub. No.: WO00/45869

PCT Pub. Date: Aug. 10, 2000

(30) Foreign Application Priority Data

Feb. 2, 1999 (SE) ................................................ 9900345

(51) Int. Cl.[7] .......................... B05D 5/00; C08L 75/00; B32B 27/40
(52) U.S. Cl. .................. 427/245; 427/2.31; 428/423.1; 523/332; 523/105; 528/495; 528/499; 528/503
(58) Field of Search ................................ 424/425, 426; 523/113, 105, 332; 527/300; 528/495, 499, 503; 427/2.31, 245; 428/423.1

(56) References Cited

U.S. PATENT DOCUMENTS

| | | | |
|---|---|---|---|
| 3,622,526 A | * | 11/1971 | Zorn et al. |
| 3,644,233 A | * | 2/1972 | Traubel et al. |
| 4,704,130 A | * | 11/1987 | Gilding et al. |
| 5,514,378 A | * | 5/1996 | Mikos et al. ............... 424/425 |
| 5,521,273 A | * | 5/1996 | Yilgör et al. |
| 5,629,402 A | * | 5/1997 | Pedain et al. |
| 6,210,441 B1 | * | 4/2001 | Flodin ..................... 623/13.18 |

FOREIGN PATENT DOCUMENTS

| | | |
|---|---|---|
| SE | 505703 | 9/1997 |
| WO | 8601095 | 2/1986 |
| WO | WO 97/22643 | 6/1997 |

* cited by examiner

*Primary Examiner*—Tae H. Yoon
(74) *Attorney, Agent, or Firm*—Lerner, David, Littenberg, Krumholz & Mentlik, LLP

(57) ABSTRACT

Porous films for medical use are provided comprising linear block polymers of polyurethane and urea containing hydrolyzable ester groups which are spaced along the carbon chain backbone of the film predetermined distances, so that upon hydrolysis of the ester groups fragments of the polymer are formed which have a size which can be secreted from the body of a mammal, the porous film including pores having an average pore size of up to 600 μm.

15 Claims, No Drawings

FILM FOR MEDICAL USE, CONSISTING OF LINEAR BLOCK POLYMERS OF POLYURETHANE AND A METHOD FOR THE PRODUCTION OF SUCH A FILM

FIELD OF THE INVENTION

The present invention relates to a film for medical use, which film consists of linear block polymers of polyurethane and urea containing groups which can behydrolyzed. More particularly, the present invention relates to a porous film, and is designed to be used as a temporary implant after operations on, or damage to, a human body or a mammal. More particularly, the present invention relates to a procedure for obtaining the desired porosity.

BACKGROUND OF THE INVENTION

The healing of living tissue after an operation or damage incorporates complicated processes which are set in motion, involving a range of different cell types. In rough outline, the following processes take place in the following order: first a matrix of fibrin is formed, then the epicells begin to divide and bridge over the injury. Under the epithelial layer fibroblasts are already beginning to build connective tissue consisting of collagen and base substances. The connective tissue is gradually vascularized and condensed into scar tissue.

In other cases, for example in the healing of broken bones, the formation of the matrix is followed by the growth of stem cells, which are categorized as chondroblasts. These form soft callus, consisting of cartilage, in the fracture. Fibroblasts migrate into the cartilage and form zones of collagen. Then osteoblasts enter and form new spongy bone. The final phase in the healing process consists of the conversion to hard bone and restoration of the remaining structure. This can take years before it is completed.

Even if the healing process goes generally well, its complicated course creates many possibilities for going wrong. For example, micro-organisms can affect it or a wounded area can act together with wrong "neighboring areas" and form a joint growth. Often there are fibroblasts which grow quickly and are a source of unwanted connective tissue formation. This can prevent reconstruction of bone tissue or other desired tissue.

Therefore, there has long been a wish to be able to assist the self-healing process and overcome the problems set forth above.

SUMMARY OF THE INVENTION

This and other objects have now been realized by the invention of a porous film for medical use comprising a linear block polymer of polyurethane and urea containing hydrolyzable ester groups and having a carbon chain backbone, the hydrolyzable ester groups being spaced along the carbon chain backbone a predetermined distance such that upon hydrolysis of the ester groups fragments of the polymer are formed having a size which can be secreted from the body of a mammal, the porous film including pores having an average pore size of up to 600 $\mu$m. In a preferred embodiment, the porous film has a predetermined thickness, and the porosity of the film varies across the thickness. Preferably, the porosity of the film is asymmetric across the thickness of the film.

In accordance with one embodiment of the porous film of the present invention, a mesh of biodegradable material is laminated to the porous film.

In accordance with another embodiment of the porous film of the present invention, the film forms a coating on individual threads of a biodegradable fabric.

In accordance with the present invention, a method has also been devised for the preparation of a porous film for medical use comprising preparing a solution of a linear block polymer of polyurethane and urea containing hydrolyzable ester groups at a concentration of between 5% and 30% in a solvent, applying a thin layer of the solution onto a surface, and treating the coated surface by evaporating the solvent or treating the layer with a polymer precipitating agent. In a preferred embodiment, the concentration of the polymer in the solvent is between 10% and 20%.

In accordance with one embodiment of the method of the present invention, the polymer precipitating agent is water, methanol or acetone.

In accordance with another embodiment of the method of the present invention, the method includes controlling the size of pores of the porous film. In a preferred embodiment, controlling of the size of the pores comprises adjusting the polymer concentration, selecting the solvent having a predetermined volatility, selecting the temperature during the process, or selecting the time of the process of evaporating and treating.

In accordance with one embodiment of the method of the present invention, the solvent comprises a mixture of a plurality of solvents. In a preferred embodiment, the method includes controlling the size of the pores by selecting the plurality of solvents having a corresponding plurality of volatilities.

In accordance with another embodiment of the method of the present invention, the method includes adjusting the pore size of the pores by conditioning the porous film during the carrying out of the method. In a preferred embodiment, the conditioning comprises immersion of the porous film in at least one solvent or thermal treatment of the porous film. Preferably, the method includes immersion of the porous film in a mixture of solvents and anti-solvents.

According to the present invention, a porous film has been provided which can be used for medical purposes consisting of linear block polymers of polyurethane and urea containing hydrolyzable ester groups at such a spacing in the carbon chain that on hydrolysis of the ester groups such small fragments are formed that they can be secreted from a human body, or that of a mammal, which film is characterised in that it is porous with an average pore size up to 600 $\mu$m.

According to the present invention, the film is further characterized in that the porosity can be varied across the thickness of the film.

According to the present invention, the porosity through the thickness of the film can be asymmetric, i.e. a thin outer layer has lower porosity.

According to the present invention, it is often appropriate that the film is laminated with a mesh of biodegradable material.

According to the present invention, the film can be made up of a coating on the individual threads in a biodegradable mesh or the like.

The present invention also includes a method for the production of a porous film for medical use consisting of linear block polymers of polyurethane containing hydrolyzable ester groups, in which procedure a solution of the polymers with a concentration of 5 to 30% is applied in a thin layer on a surface, after which the solvent is evaporated and/or the layer is treated with a polymer-precipitating agent.

According to the present invention, the precipitating agent can be best chosen from the group consisting of water, methanol and acetone.

According to the present invention, the porosity is adjusted by means of the polymer concentration, where high concentrations give small pores, by means of the solvent, where highly volatile solvents give small pores, by means of temperature, where high temperatures give small pores and/or time, where short evaporation or precipitation times, as appropriate, give small pores.

According to the present invention, a mixture of two or more solvents with different volatilities can be used to effect variable porosity through the film thickness.

According to the present invention, the porosity of the film can also be adjusted by the conditioning of an already-formed film by immersing it in a solvent or a mixture of solvents and non-solvents and/or by heat treatment.

Porous films can assist in preventing undesired growth of cells by acting as a barrier over a wound area. In addition, porous films can be used to repair or replenish a periosteum in the case of transplants of e.g. cartilage. The porosity allows transport of dissolved substances, such as metabolites and/or proteins through the film. If the pore size is sufficient certain cell types can also grow in the film. Films with very large pores can also permit vascularization. For these various processes the following limiting values for the average pore sizes can be given:

<1 µm diffusion of dissolved components and growth of collagen,

<5 µm no growth of fibrous tissue,

<15 µm relatively little growth of fibrous tissue,

40–200 µm growth of fibrous tissue plus vascularization,

>600 µm reduced growth of cells and necrosis of tissue.

The polymer used in the present films is degradable into harmless substances which are eliminated from the body by secretion or metabolizing. According to the present invention, the time for degradation is not too short so that one is able to avoid locally high concentrations of degradation products. The speed of degradation is also varied in order to suit the need in various applications.

The requirements for the mechanical properties of the films hereof can vary depending on the application. In many applications the tear strength is especially important, e.g. when the films are to be fixed with pins or the like or sewn firmly. In cases which are very demanding, the modulus of elasticity, tear strength, etc. can be improved by laminating the film to a mesh of biodegradable fibers. Alternatively, the mesh can be impregnated or coated with a solution or dispersion of the polymer with subsequent removal of the solvent.

DETAILED DESCRIPTION

It has become evident that porous films and sheets with the desired properties can be produced from polymers of the type linear block polymers of polyurethane urea. Suitable polymers are produced by the use of diisocyanates, diols and carbon chain lengtheners according to methods known for the specific components. In order to form films the molecular weight of the polymers should be >10,000 Daltons, preferably >100,000 Daltons.

A convenient technique to produce the polymers is to use the so-called pre-polymerization technique, i.e. first produce an isocyanate-terminated pre-polymer and thereafter lengthen its carbon chain with a diamine so that the desired molecular weight is obtained. The equations for the reaction can be written as:

$$2\ OCN-R_1-NCO + HO-R_2-OH \rightarrow OCN-R_1-NHCO-O-R_2-O-CONH-R_1-NCO \quad (1)$$

$$OCN-R_1-NHCO-O-R_2-O-CO-NH-R_1-NCO + NH_2-R_3-NH_2 \cdots \rightarrow [-CONH-R_1-NHCO-O-R_2-O-CONH-R_1-NHCONH-R_3-NH-]_n- \quad (2)$$

where at least one of $R_1$, $R_2$ and $R_3$ must contain one or more ester groups in the carbon chain in order to meet the requirement for degradability into small fragments. It is also possible to use mixtures of several pre-polymers in order to achieve special effects, e.g. to introduce groups which can react after polymerization to introduce physiologically active groups into the polymers. In addition, small quantities of carbon chain terminators can be added to limit the upper molecular weight.

The diisocyanates which can be used are diphenylmethane-4,4'-diisocyanate (MDI), dicyclohexylmethane-4,4'-diisocyanate, cyclohexyl-1,4-diisocyanate, toluylene diisocyanate and many more commercially available diisocyanates and laboratory-produced species, e.g. those based on amino acids, such as 1-lysine methyl ester diisocyanate.

The diolefines used can be simple aliphatics, such as ethylene glycol, diethylene glycol or higher oligomers, tetramethylene oxide glycol or higher oligomers, diol esters such as oligocaprolactone diol, oligoethylene glycol adipate diol, oligodiethylene glycol adipate, dimethylol propionic acid, dimethylol propionic acid methyl ester, trimethylol propane monoallyl ether and many more.

Carbon chain extenders can be simple diamines, such as ethylene diamine, 1,3-propylene diamine or 1,2-propylene diamine. They can also contain ester groups in the carbon chain in order to permit degradation by hydrolysis. It is possible and often expedient to use mixtures of carbon chain extenders.

Primary or secondary monoamines can be used as carbon chain terminators, e.g. diethylamine, morpholine or propylamine. Here also, mixtures can be expedient.

Reaction (1) in the reaction scheme set forth above can be carried out in bulk at elevated temperatures e.g. 70 to 80° C. for MDI or 100 to 110° C. for dicyclohexylmethane diisocyanate. In the presence of a catalyst the reactions can be carried out at significantly lower temperatures. However, reaction (2), the carbon chain lengthening, is performed in solution on account of the high speed of reaction and the gelling tendency of the polymer formed. The resulting polymer solution can be used directly or after dilution for the production of a film or sheet. In certain solvents, e.g. acetone, the polymer so formed is precipitated and can be filtered off and then re-dissolved in a solvent for the same, e.g. dimethyl formamide, dimethyl sulphoxide or dimethyl acetamide.

The films of the present invention are formed from solutions which are applied as thin layers on a planar surface, after which the solvent is evaporated and/or the film is treated with a precipitating agent. To obtain a porous film the polymer concentration must be from 5 to 30%, preferably 10 to 20%. After application the solvent can be wholly or partially evaporated or removed by addition of an anti-solvent. Examples of such anti-solvents are water, methanol and acetone.

A prerequisite for porosity is that the polymer solution at some stage of removal of the solvent forms a gel, i.e. coagulates. Polymers according to the present invention have a pronounced tendency for coagulation by the strong interaction of the blocks by means of phase separation and hydrogen bonding. Important other factors, which favor gel formation, are high polymer concentration and high molecular weight.

Pore size and pore size distribution can be adjusted with concentration and the precipitation conditions associated with addition of the anti-solvent. Alternatively, a pre-produced film can be conditioned with solvent, mixtures of solvents and anti-solvents and/or thermal treatment. Conditioning is carried out by dipping a pre-produced film into a solvent which is later allowed to evaporate or by warming, whereby the film swells up. In this manner, the pore sizes and their distribution are adjusted to the desired values.

The films according to the present invention can be produced from polymer solutions in several ways. The simplest way is by means of piece-by-piece production on a surface, e.g. a glass plate, onto which a layer of polymer solution of controlled thickness is spread with an applicator, after which the solvent is removed by evaporation or precipitation under carefully controlled conditions. Continuous production can be carried out by applying the polymer solution to a moving band which carries the material to a zone for precipitation and thereafter to one or more zones for post treatment and final removal of the film from the band, which is then returned.

The film strength can be increased by stretching. This causes orientation of the polymer molecules and alteration of the sizes and form of the pores. As a result, the strength increases in the direction of stretching. With biaxial stretching the strength in two dimensions can be increased.

An alternative way of increasing the strength of the films of the present invention is to combine them with a mesh of degradable fibers of, for example, polyurethane and urea according to the description in Swedish Patent No. 505,703. This patent discloses that the mesh can be partly laminated with a previously prepared film or impregnated or the mesh strengthened with polymer solution followed by evaporation of solvent and/or precipitation according to the methods described above.

A method of producing a porous film on curved surfaces is by dipping. For this a film former, such as a pipe sealed at one end, is dipped into a polymer solution. The film former is taken out, and the polymer is converted to the solid form by evaporation of solvent and/or coagulation with an anti-solvent. The procedure can be repeated until the desired film thickness is obtained, after which the film is slid off the former.

The present invention may also be more fully appreciated with reference to the following examples.

EXAMPLE 1

A pre-polymer was produced by reacting diphenylmethane diisocyanate (MDI) with polycaprolactone diol (molecular weight 530) in the molar ratio of 2:1 at 70 to 80° C. for 2 hours. 32.35 g of the resulting pre-polymer were dissolved in 138 g of dimethyl formamide (DMF) and the chain extended with 2.35 g of 1,3 diaminopropane and 0.08 g of dibutyl amine in 59 g of DMF at 0° C. The solution was diluted with 12.5% and 1% LiCl was added to reduce the viscosity.

Part of the resulting polymer solution was spread out on a glass plate to a thickness of 300 $\mu$m with the help of an applicator. Part of the solvent was evaporated in a fume cupboard at 20° C. over 20 minutes. The film whitened thereby, signifying phase separation. The remainder of the solvent was then removed by washing with water. The film so formed was examined using a scanning electron microscope (SEM) and exhibited throughpores with an average diameter of 2 $\mu$m.

EXAMPLE 2

Part of the polymer solution of example 1 was applied to a glass plate and the solvent evaporated in a fume cupboard at 20° C. for 14 hours. The residual DMF was washed away with water. The film so formed had a throughpore structure with pore sizes between 2 and 7 $\mu$m.

EXAMPLE 3

Part of the polymer solution of example 1 was applied to a glass plate and immersed in acetone for 10 minutes, whereby the polymer separated out. The acetone and residual DMF were washed away with water. The film so formed had a throughpore structure with pore sizes around 1 $\mu$m.

EXAMPLE 4

Part of the polymer solution of example 1 was applied to a glass plate. Part of the solvent was evaporated by warming the glass plate in two minutes up to 100° C. The remaining solvent was evaporated in a fume cupboard in one hour at 20° C. The film so formed was washed with water to take away the remaining DMF. The film so formed had a throughpore structure with pore sizes between 2 and 7 $\mu$m.

EXAMPLE 5

12.3 g of the pre-polymer obtained in example 1 were dissolved in 52.5 g of dimethyl formamide (DMF) and had the chain extended with 0.9 g of 1,3-diaminopropane and 0.06 g of dibutylamine in 22.5 g of DMF at 20° C.

Part of the resulting polymer solution was applied to a glass plate to a thickness of 500 $\mu$m with the help of an applicator. The solvent was evaporated in a fume cupboard for 14 hours at 20° C. The residual DMF was washed away with water.

EXAMPLE 6

A pre-polymer was produced by reacting dicyclohexane methane diisocyanate ($H_{12}$MDI) with polycaprolactone diol (molecular weight 530) in the molar ratio 2:1 at 100–110° C. for four hours. Additionally, a pre-polymer was produced by reacting $H_{12}$MDI with dimethylolpropionic acid in the ratio 2:1 in dimethyl sulphoxide (DMSO) at 75 to 80° C. for one hour. 26 g of pre-polymer 1 and 8.7 g of pre-polymer 2+DMSO were dissolved in 66 g of DMSO and the chain extended with 2.12 g of 1,3-diaminopropane in 20 g of DMSO at 20° C.

Part of the resulting polymer solution was applied to a glass plate to a thickness of 300 $\mu$m with the help of an applicator. The solvent was evaporated in a fume cupboard for 14 hours at 20° C. The residual DMF was washed away with water.

EXAMPLE 7

A pre-polymer was produced by reacting diphenylmethane diisocyanate (MDI) with polydiethyleneglycol adipate (molecular weight 550) in the molar ratio 2:1 at 70 to 80° C. for two hours. 13.2 g of the resulting pre-polymer were dissolved in 34 g of dimethylformamide (DMF) and the chain extended with 0.68 g of 1,3-diaminopropane and 0.05 g dibutylamine in 22 g of DMF at 20° C.

Part of the resulting polymer solution was applied to a glass plate to a thickness of 500 $\mu$m with the help of an applicator. The solvent was evaporated in a fume cupboard for 14 hours at 20° C. The residual DMF was washed away with water.

EXAMPLE 8

A pre-polymer was produced by reacting diphenylmethane diisocyanate (MDI) with 3-allyloxy-1,2-propane diol in the molar ratio 2:1 at 70 to 80° C. for two hours. 6.12 g of the resulting pre-polymer and 17.62 g of the pre-polymer prepared in example 7 were dissolved in 65 g of dimethyl sulphoxide (DMSO) and the chain extended with 2.17 g of 1,2-diaminopropane plus 0.07 g of ethylamine in 3.5 g of acetone and 30 g of DMSO at 20° C. The resulting polymer solution was diluted to 15% concentration by addition of 35 g DMSO.

Part of the resulting polymer solution was applied to a glass plate to a thickness of 500 μm with the help of an applicator. The solvent was evaporated in a fume cupboard for 14 hours at 20° C. The residual DMSO was washed away with water.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A porous film for medical use comprising a linear block polymer of polyurethane and urea containing hydrolyzable ester groups and having a carbon chain backbone, said hydrolyzable ester groups being spaced along said carbon chain backbone a predetermined distance such that upon hydrolysis of said ester groups fragments of said polymer are formed having a size which can be secreted from the body of a mammal, said porous film including pores having an average pore size of up to 600 μm.

2. The porous film of claim 1 wherein said porous film has a predetermined thickness, and wherein said porosity of said film varies across said thickness.

3. The porous film of claim 2 wherein said porosity of said film is asymmetric across said thickness of said film.

4. The porous film of claim 1 including a mesh of biodegradable material laminated to said porous film.

5. The porous film of claim 1 wherein said film forms a coating on individual threads of a biodegradable fabric.

6. A method for the preparation of a porous film for medical use, wherein said porous film including pores having an average pore size of up to 600 μm, comprising preparing a solution of a linear block polymer of polyurethane and urea containing hydrolyzable ester groups at a concentration of between 5% and 30% in a solvent, applying a thin layer of said solution onto a surface, and treating said coated surface by means of a process selected from the group consisting of evaporating said solvent and treating said layer with a polymer precipitating agent.

7. The method of claim 6 wherein said concentration of said polymer in said solvent is between 10% and 20%.

8. The method of claim 6 wherein said polymer precipitating agent is selected from the group consisting of water, methanol and acetone.

9. The method of claim 6 including controlling the size of pores of said porous film.

10. The method of claim 9 wherein said controlling of said size of said pores comprises a control method selected from the group consisting of adjusting said polymer concentration, selecting said solvent having a predetermined volatility, selecting the temperature during said process, and selecting the time of said process selected from the group consisting of evaporating and treating.

11. The method of claim 6 wherein said solvent comprises a mixture of a plurality of solvents.

12. The method of claim 11 including controlling the size of said pores by selecting said plurality of solvents having a corresponding plurality of volatilities.

13. The method of claim 6 including adjusting the pore size of said pores by conditioning of said porous film during the carrying out of said method.

14. The method of claim 13 wherein said conditioning comprises a conditioning step selected from the group consisting of immersion of said porous film in at least one solvent and thermal treatment of said porous film.

15. The method of claim 14 including immersion of said porous film in a mixture of solvents and anti-solvents.

* * * * *

UNITED STATES PATENT AND TRADEMARK OFFICE
CERTIFICATE OF CORRECTION

PATENT NO.    : 6,627,258 B1
DATED         : September 30, 2003
INVENTOR(S)   : Flodin et al.

It is certified that error appears in the above-identified patent and that said Letters Patent is hereby corrected as shown below:

<u>Title page,</u>
Item [86], PCT Date, delete "2000" and insert -- 2001 --.

Signed and Sealed this

Eighteenth Day of November, 2003

JAMES E. ROGAN
*Director of the United States Patent and Trademark Office*